(12) United States Patent
Al-Qasim et al.

(10) Patent No.: US 11,454,077 B2
(45) Date of Patent: *Sep. 27, 2022

(54) SYSTEMS AND METHODS FOR CORE FLOODING

(71) Applicant: Saudi Arabian Oil Company, Dhahran (SA)

(72) Inventors: Abdulaziz Al-Qasim, Dammam (SA); Taha Okasha, Alkhobar (SA)

(73) Assignee: Saudi Arabian Oil Company, Dhahran (SA)

( * ) Notice: Subject to any disclaimer, the term of this patent is extended or adjusted under 35 U.S.C. 154(b) by 83 days.

This patent is subject to a terminal disclaimer.

(21) Appl. No.: 16/892,977

(22) Filed: Jun. 4, 2020

(65) Prior Publication Data
US 2021/0381328 A1 Dec. 9, 2021

(51) Int. Cl.
*E21B 25/06* (2006.01)
*G01N 15/08* (2006.01)
(Continued)

(52) U.S. Cl.
CPC ......... *E21B 25/06* (2013.01); *G01N 15/0806* (2013.01); *G01N 15/0826* (2013.01); *G01N 33/241* (2013.01); *E21B 43/20* (2013.01)

(58) Field of Classification Search
CPC .......................... E21B 25/06; G01N 15/0806; G01N 15/0826; G01N 33/241
See application file for complete search history.

(56) References Cited

U.S. PATENT DOCUMENTS 4,380,930 A * 4/1983 Podhrasky ............. G01N 29/11
367/13
4,631,963 A * 12/1986 Sprunt .................. E21B 49/006
367/13
(Continued)

FOREIGN PATENT DOCUMENTS

CN 108286423 7/2018
CN 110107273 8/2019
(Continued)

OTHER PUBLICATIONS

English Machine Translation of CN 110529107 A (Year: 2021).*
(Continued)

*Primary Examiner* — John Fitzgerald
(74) *Attorney, Agent, or Firm* — Fish & Richardson P.C.

(57) ABSTRACT

A core flooding system includes a core holder that encloses a core sample of a subterranean formation. The core holder includes a fluid inlet and a fluid outlet; at least one sensor coupled to the core holder or positioned in the inner volume of the core holder; an acoustic vibrating assembly coupled to the core holder; and a control system communicably coupled to the at least one sensor and the acoustic vibrating assembly. The control system performs operations including operating the acoustic vibrating assembly to transmit at an acoustic wave energy or a vibration energy to the core holder; during the transmission of the at least one of the acoustic wave energy or the vibration energy to the core holder; measuring at least one parameter of the core sample; and based on the at least one measured parameter, determining at least one property of the core sample.

30 Claims, 5 Drawing Sheets

(51) Int. Cl.
  *G01N 33/24* (2006.01)
  *E21B 43/20* (2006.01)

(56) References Cited

U.S. PATENT DOCUMENTS

| | | | | |
|---|---|---|---|---|
| 5,178,005 A * | 1/1993 | Peterson | ............... | G01N 33/24 |
| | | | | 73/152.11 |
| 5,265,461 A * | 11/1993 | Steiger | ............... | G01N 29/07 |
| | | | | 73/594 |
| 5,868,030 A * | 2/1999 | Brumley | ............... | G01N 29/227 |
| | | | | 73/784 |
| 6,814,141 B2 | 11/2004 | Huh et al. | | |
| 7,352,179 B2 | 4/2008 | Chen et al. | | |
| 7,853,045 B2 | 12/2010 | Touati et al. | | |
| 9,133,709 B2 | 9/2015 | Huh et al. | | |
| 10,107,056 B2 | 10/2018 | Zhang et al. | | |
| 10,184,904 B1 | 1/2019 | Gong et al. | | |
| 10,845,291 B2 * | 11/2020 | Kanj | ............... | G01N 33/241 |
| 10,851,641 B2 * | 12/2020 | Yang | ............... | E21B 47/18 |
| 10,920,574 B1 * | 2/2021 | Yang | ............... | G01N 33/24 |
| 2009/0110242 A1 | 4/2009 | Touati et al. | | |
| 2016/0109603 A1 * | 4/2016 | Jin | ............... | E21B 49/06 |
| | | | | 73/152.58 |
| 2018/0335374 A1 * | 11/2018 | Kanj | ............... | G01N 15/0826 |
| 2022/0090460 A1 * | 3/2022 | Al-Qasim | ............... | G01N 15/0806 |

FOREIGN PATENT DOCUMENTS

| | | | |
|---|---|---|---|
| CN | 110243692 A | * | 9/2019 |
| CN | 110529107 | | 12/2019 |

OTHER PUBLICATIONS

English Machine Translation of CN 108286423 (Year: 2021).*
Ragab et al. "The Effect of Ultrasonic Waves of EOR on the Relative Permeability Curves," SPE-175410-MS (Year: 2015).*
PCT International Search Report and Written Opinion in International Appln. No. PCT/US2021/035644, dated Sep. 22, 2021, 15 pages.
Mullakaev et al., "Development of ultrasonic equipment and technology for well stimulation and enhanced oil recovery," Journal of Petroleum Science and Engineering, 2015, 125: 201-208.
Westermark et al., "Enhanced Oil Recovery with Downhole Vibration Stimulation," SPE 67303, presented at the SPE Production and Operations Symposium, Oklahoma City, Oklahoma, Mar. 24-27, 2001; Society of Petroleum Engineers, 2001, 13 pages.
Yousef et al., "Laboratory Investigation of the Impact of Injection-Water Salinity and Ionic Content on Oil Recovery for Carbonate Reservoirs," SPE 137634-PA, Society of Petroleum Engineers, Oct. 2011, 14(5): 1-5.

* cited by examiner

SYSTEMS AND METHODS FOR CORE FLOODING

TECHNICAL FIELD

This disclosure relates to systems and method for core flooding and, more particularly, systems and methods for core flooding while subjecting a core sample to wave energy.

BACKGROUND

In the oil and gas industry, core holders are used mainly to simulate flooding experiments that can provide valuable measurements related to oil and gas recovery, fluid permeability, and flow properties. The core flooding experiments are generally conducted at high pressure and temperature representing reservoir conditions.

SUMMARY

This disclosure describes systems and methods for core flooding of a core sample in a core flooding system that includes, for example, one or more sub-assemblies that generate and transmit vibration energy or acoustic wave energy (or both) to the core sample. In some aspects, the one or more sub-assemblies may generate and transmit such energy directly to the core sample. In some aspects, the one or more sub-assemblies may generate and transmit such energy indirectly to the core sample. Measurements of one or more parameters of the core sample may be taken during such transmission of energy. The measured parameter(s) may be used to determine one or more properties of the core sample, and consequently, a reservoir formation from which the core sample is taken.

In an example implementation, a core flooding system includes a core holder that includes a housing that defines an inner volume sized to enclose a core sample of a subterranean formation, the core holder further including a fluid inlet and a fluid outlet; at least one sensor coupled to the core holder or positioned in the inner volume of the core holder; an acoustic vibrating assembly coupled to the core holder; and a control system communicably coupled to the at least one sensor and the acoustic vibrating assembly. The control system is configured to perform operations including operating the acoustic vibrating assembly to transmit at least one of an acoustic wave energy or a vibration energy to the core holder; during the transmission of the at least one of the acoustic wave energy or the vibration energy to the core holder; measuring at least one parameter of the core sample with the at least one sensor; and based on the at least one measured parameter, determining at least one property of the core sample.

In an aspect combinable with the example implementation, the acoustic vibrating assembly includes a mechanical vibrator mounted on a platform, the mechanical vibrator coupled to the core holder.

In another aspect combinable with any of the previous aspects, the platform includes at least one rotating plate to which the core holder is mounted.

In another aspect combinable with any of the previous aspects, the control system is configured to perform operations further including operating the at least one rotating plate to rotate the core holder about an axis.

In another aspect combinable with any of the previous aspects, the axis includes a first axis, the control system configured to perform operations further including operating the at least one rotating plate to rotate the core holder about a second axis.

In another aspect combinable with any of the previous aspects, operating the at least one rotating plate to rotate the core holder about the second axis is performed simultaneously with operating the at least one rotating plate to rotate the core holder about the first axis.

Another aspect combinable with any of the previous aspects further includes at least one spring mounted to the mechanical vibrator.

In another aspect combinable with any of the previous aspects, the acoustic vibrating assembly includes at least one perforated rod that includes an airflow path; and at least one balloon fluidly coupled to the airflow path through the perforated rod.

In another aspect combinable with any of the previous aspects, the control system is configured to perform operations further including flowing a gas through the airflow path to inflate the at least one balloon to induce the vibration energy through the core holder.

Another aspect combinable with any of the previous aspects further includes a sleeve mountable within the inner volume and sized to hold the core sample, the acoustic vibrating assembly including a vibrator mounted within the sleeve to impart the at least one of the acoustic wave energy or the vibration energy to the core sample.

In another aspect combinable with any of the previous aspects, the acoustic vibrating assembly includes a noise source positionable apart from the core holder, the control system configured to perform operations further including operating the noise source to generate the acoustic wave energy.

Another aspect combinable with any of the previous aspects further includes at least one valve fluidly coupled to at least one of the fluid inlet or the fluid outlet.

In another aspect combinable with any of the previous aspects, the control system is configured to perform operations further including operating the at least one valve to flow a fluid through the inner volume of the core holder.

In another aspect combinable with any of the previous aspects, the operation of operating the at least one valve to flow the fluid through the inner volume of the core holder occurs simultaneously with operating the acoustic vibrating assembly to transmit at least one of the acoustic wave energy or the vibration energy to the core holder.

In another example implementation, a method for testing a core sample includes positioning a subterranean formation core sample in an inner volume of a core holder, the core holder including a housing that defines the inner volume, a fluid inlet, and a fluid outlet; transmitting at least one of an acoustic wave energy or a vibration energy to the core holder; during the transmission of the at least one of the acoustic wave energy or the vibration energy to the core holder; measuring at least one parameter of the core sample with at least one sensor coupled to the core holder or positioned in the inner volume of the core holder; and based on the at least one measured parameter, determining at least one property of the core sample.

In an aspect combinable with the example implementation, transmitting at least one of the acoustic wave energy or the vibration energy to the core holder includes operating a mechanical vibrator coupled to the core holder and mounted on a platform.

Another aspect combinable with any of the previous aspects further includes rotating the core holder about an axis with at least one rotating plate to which the core holder is mounted.

In another aspect combinable with any of the previous aspects, the axis includes a first axis, the method further including rotating the core holder about a second axis with the at least one rotating plate.

In another aspect combinable with any of the previous aspects, rotating the core holder about the first and second axes occurs simultaneously.

In another aspect combinable with any of the previous aspects, transmitting at least one of the acoustic wave energy or the vibration energy to the core holder includes flowing a fluid through an airflow path of at least one perforated rod coupled to the core holder; inflating at least one balloon fluidly coupled to the airflow path through the perforated rod; and based on inflating the at least one balloon, transmitting at least one of the acoustic wave energy or the vibration energy to the core holder.

Another aspect combinable with any of the previous aspects further includes, while transmitting at least one of the acoustic wave energy or the vibration energy to the core holder, inflating at least one balloon mounted to the core holder; and based on inflating the at least one balloon, tilting the core holder.

In another aspect combinable with any of the previous aspects, transmitting at least one of the acoustic wave energy or the vibration energy to the core holder includes vibrating the core sample with a vibrator mounted to or within a sleeve that holds the core sample to impart the at least one of the acoustic wave energy or the vibration energy to the core sample.

In another aspect combinable with any of the previous aspects, transmitting at least one of the acoustic wave energy or the vibration energy to the core holder includes generating the acoustic wave energy with a noise source positioned apart from the core holder.

Another aspect combinable with any of the previous aspects further includes modulating at least one valve fluidly coupled to at least one of the fluid inlet or the fluid outlet; and circulating a fluid through the inner volume of the core holder to contact the core sample.

In another example implementation, a core sample test apparatus includes a housing sized to receive a core sample that includes a portion of a hydrocarbon reservoir formation; means for generating at least one of an acoustic wave energy or a vibration energy to the core holder; at least one sensor positioned to detect a change in at least one parameter of the core sample during operation of the means for generating the at least one of the acoustic wave energy or the vibration energy; and a control system communicably coupled to the at least one sensor and configured to receive the change in the at least one parameter of the core sample and determine at least one property of the hydrocarbon reservoir formation.

In an aspect combinable with the example implementation, the control system is operably coupled to the means for generating.

Another aspect combinable with any of the previous aspects further includes means for rotating the core sample.

In another aspect combinable with any of the previous aspects, the control system is operably coupled to the means for rotating.

In another aspect combinable with any of the previous aspects, the at least one parameter of the core sample includes at least one of a flow rate of a fluid through the core sample; an interfacial tension; a contact angle between a fluid and the core sample; a fluid path of water or brine through the core sample; or a fluid path of a hydrocarbon through the core sample.

In another aspect combinable with any of the previous aspects, the at least one property of the hydrocarbon reservoir formation a permeability of the hydrocarbon reservoir formation; a brine permeability of the hydrocarbon reservoir formation; or a porosity of the hydrocarbon reservoir formation.

In another aspect combinable with any of the previous aspects, the sensor includes a fiber optic conductor mounted within a sleeve configured to hold the core sample in the housing.

Implementations of a core flooding system according to the present disclosure may include one or more of the following features. For example, the core flooding system may monitor changes in an environment in which a core sample is tested under vibration and seismicity effects. As another example, the core flooding system may more efficiently and precisely monitor preferred paths of water, oil, and gases through a core sample under vibration and seismicity effects. As still a further example, the core flooding system may provide a better estimation for a permeability continuous profile, which is not possible by conventional techniques, and compare this profile with the brine permeability results. For example, the core flooding system may include one or more sensors to measure certain parameters, such as differential pressure of each phase of a multiphase fluid within (or flowing through) the core sample to evaluate a permeability profile of the core sample.

Implementations of a core flooding system according to the present disclosure may also include one or more of the following features. For example, the core flooding system may better assess future enhanced oil recovery (EOR) processes, injectivity, and water shut off jobs as compared to conventional techniques. As another example, the core flooding system may better assess certain parameters (such as interfacial tension and contact angle) that are helpful for hydrocarbon reserve evaluation and fluids distribution in oil and gas reservoirs as compared to conventional techniques. Also, the core flooding system may reduce an amount of time, money, and risk associated with such completion techniques by providing more accurate reservoir information. As another example, the core flooding system may facilitate assessment of parameters that allow evaluation of a fluid distributions in a transition zone, a remaining oil saturation post water flooding, and an additional oil recovery as a result of an EOR injectant.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

Figure 1:
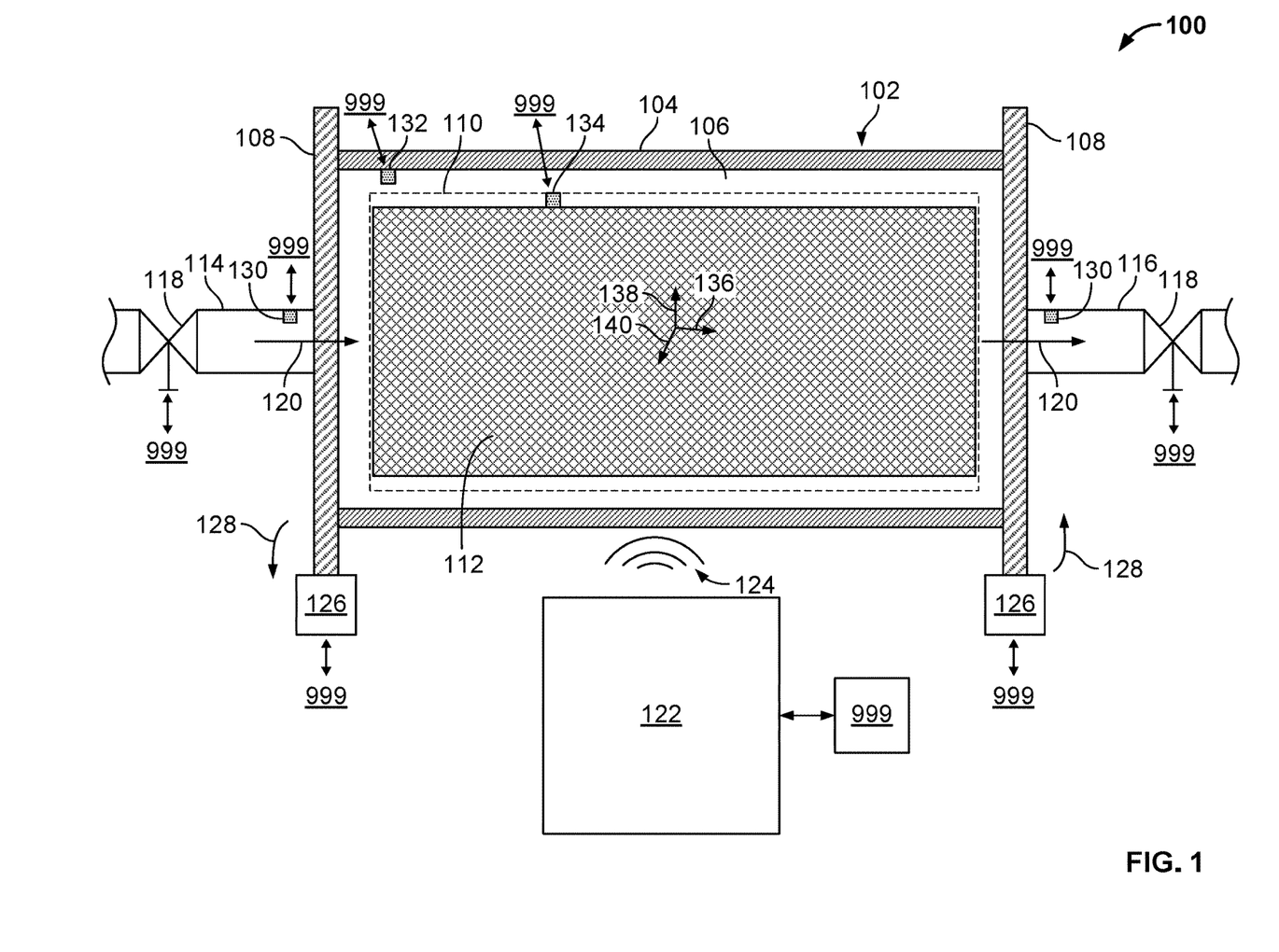
FIG. 1 is a side cross-section of a schematic diagram of an example implementation of a core flooding system according to the present disclosure.

FIG. 1 is a side cross-section of a schematic diagram of an example implementation of a core flooding system 100 according to the present disclosure. Generally, the core flooding system 100 may operate to analyze a core sample 112, as well as a fluid flow through the core sample 112, under various and varying conditions, including a wide range of vibrational frequencies, acoustic wave energy, rotation and tilting, and convention varying conditions such as temperature and pressure. In some aspects, the use of vibration to improve oil recovery has been implemented, with successful vibration stimulation in shallow reservoirs with high water-to-oil ratios (WOR). Laboratory and pre-pilot field-testing of a vibration impact, for example, to simulate such conditions, has been lacking. The core flooding system 100 implements such conditions using vibro-seismic technology that generates vibrational energy, acoustic wave energy, or both.

As shown in this example implementation, the core flooding system 100 includes a core holder 102 that is comprised of a housing 104 (for example, a cylindrical housing) that may be enclosed on open ends by end plates 108 to define an inner volume 106. The core sample 112 may be inserted into the inner volume 106 (and enclosed there by the housing 104 and the plates 108). In some aspects, as shown, a sleeve 110 (for example, a flexible sleeve) may be used to hold the core sample 112 in the inner volume 106.

In this example, a fluid inlet 114 is positioned through one end plate 108 while a fluid outlet 116 is positioned through another end plate 108. A fluid 120 (such as water, oil, gas, or a mixture thereof) may be circulated through the inner volume 106 and saturate or contact the core sample 112. As shown in this example, valves 118 may be positioned on both of the inlet 114 and the outlet 116 to control a flow of the fluid 120.

Like conventional core flooding systems, the core flooding system 100 may conduct core flooding and interfacial tension contact angle tests that mimic reservoir conditions (for example, pressure, temperature, and reservoir fluids). In some aspects, the core flooding system 100 may apply a constant pressure across the end plates 108 or constant flow through the end plates 108 (or core plugs, not shown). Core flood tests can be conducted using single or multiple core holders to acquire critical reservoir properties such as permeability contrasts and fluid movement in porous media. Core flooding results may then be used to guide mathematical models and extract critical simulation parameters. While helpful, such conventional tests (which still may be performed by the core flooding system 100), may not take into consideration an impact of natural or imposed seismic activities as well as surface vibrations by heavy equipment. As explained more fully herein, the core flooding system 100 and other example implementations of a core flooding system according to the present disclosure may generate vibration energy, acoustic energy, or both, and measure one or more parameters associated with the core sample 112 to determine one or more geologic properties of the core sample 112 or an associated reservoir formation.

For example, as shown in FIG. 1, an acoustic vibration assembly 122 may be coupled to (for example, near, or in contact with) the core holder 102. Generally, the acoustic vibration assembly 122 may include one or more sub-assemblies that generate vibration energy, acoustic wave energy, or both and transmit such energy 124 to the core holder 102 and, subsequently, the core sample 112. In some aspects, one or more sub-assemblies of the acoustic vibration assembly 122 may be in contact with the core holder 102 and provide direct vibrational energy 124 to the core holder 102. In some aspects, one or more sub-assemblies of the acoustic vibration assembly 122 may be spaced apart from (and not in contact with) the core holder 102 and provide remote acoustic wave energy 124 to the core holder 102 and subsequently, the core sample 112. In some aspects, one or more sub-assemblies of the acoustic vibration assembly 122 may not be in direct contact with the core holder 102, but may provide direct vibrational energy to other components of the system 100 that are in contact with the core holder 102 (thereby providing indirect vibrational energy 124 to the core holder 102, and subsequently, the core sample 112).

As shown in this example, a rotation assembly 126 may also be coupled (directly or otherwise) to the core holder 102. The rotation assembly 126 may be operated to rotate or tilt the core holder 102, such as with rotation 128. In some aspects, the rotation assembly 126 may be operated to tilt or rotate the core holder 102 about an axis 136 (radial axis 136) that is coincident with a centerline radial axis of the core sample 112. In some aspects, the rotation assembly 126 may be operated to tilt or rotate the core holder 102 about an axis 138 (axial axis 138) that is orthogonal to the centerline radial axis 136 of the core sample 112. In some aspects, the rotation assembly 126 may be operated to tilt or rotate the core holder 102 about an axis 140 (axial axis 140) that is orthogonal to the centerline radial axis 136 of the core sample 112 as well as axis 138. In some aspects, the rotational assembly 126 may be operated to rotate or tilt the core holder.

In some aspects, operation of the rotation assembly 126 and the acoustic vibration assembly 122 may be simultaneous. In some aspects, operation of the rotation assembly 126 and the acoustic vibration assembly 122 may be sequential. Further, in some aspects, changes in temperature, pressure, or both, within the inner volume 106 (and thus the core sample 112) may be made in parallel with or sequentially with one or both of the rotation assembly 126 and the acoustic vibration assembly 122. Still further, changes in properties of the fluid 120 (for example, composition, pressure, temperature, and otherwise) may be made in parallel with or sequentially with one or both of the rotation assembly 126 and the acoustic vibration assembly 122, as well as in parallel with or sequentially with other conventional testing parameters (for example, temperature or pressure).

As shown in this example, the core flooding system 100 includes one or more fluid sensors 130 (in this case, two), as well as other sensors 132 and 134. In some aspects, each sensor shown in FIG. 1 may represent one or multiple sensors. Each sensor shown in FIG. 1 may also be an analog or digital sensor. In some aspects, the illustrated sensors 130, 132, and 134 may be fiber optic conductors. As shown in this example, one or more sensors 132 may be positioned within the internal volume 106 (but external to the sleeve 110). Further, in this example implementation, one or more sensors 134 may be positioned between the core sample 112 and the sleeve 110. Alternatively, sensors may be placed external to (for example, in contact with an exterior surface of) the housing 104.

The example implementation of the core flooding system 100 includes a control system 999. In some implementations, the control system 999 is a microprocessor-based control system that includes one or more hardware processors, one or more memory modules communicably coupled to the hardware processor(s), and instructions and data encoded on the one or more memory modules. The hardware processor(s) are operable to execute the instructions to perform operations, including operations described in the present disclosure. As shown in this example (for example, by the bi-directional arrows), the control system 999 may be communicably coupled (wired or wirelessly) to, for instance, the acoustic vibration assembly 122, the sensors 130, 132, and 134, and the rotation assembly 126. In some aspects, the control system 999 may receive data from the acoustic vibration assembly 122, the sensors 130, 132, and 134, and the rotation assembly 126, as well as provide commands (pre-programmed or otherwise) to the acoustic vibration assembly 122, the sensors 130, 132, and 134, and the rotation assembly 126.

For example, in an example operation, the control system 999 may command the acoustic vibration assembly 122 to operate one or more acoustic vibration sub-assemblies to generate and transmit the vibration and/or acoustic wave energy 124 to the core holder 102 (and thus the core sample 112). The control system 999 may also command the rotation assembly 126 to tilt or rotate the core holder 102 (and thus the core sample 112), either simultaneous with or sequentially with the operation of the acoustic vibration assembly 122. The control system 999 may also command one or more valves 118 to facilitate circulation of the fluid 120 into the inner volume 106 of the core holder 102 (and thus to the core sample 112), either simultaneous with or sequentially with the operation of the acoustic vibration assembly 122, the rotation assembly 126, or both. Further, the control system 999 may operate to adjust a temperature or pressure within the inner volume 106. The sensors 130, 132, and/or 134 may measure one or more parameters associated with the core sample 112, such as temperatures, confining stresses, pressures, fluid content, directional flow (for example, velocity, pathways, or both) of one or more phases of a multiphase fluid, and other parameters. In some aspects, for instance, movement (for instance, rotation, tilting, vibration) of the core holder 102 in different directions can affect the evaluation of directional permeability, vertical permeability (such as in tilted reservoirs) and can evaluate gravity drainage effects on remaining oil saturation (SOR) and additional hydrocarbon recovery in a reservoir.

Based on such measurements, the control system 999 may determine one or more properties of the core sample 112, and also a reservoir formation from which the core sample 112, was taken. Such properties include, for example, porosity, grain density, directional permeability, and other properties. In some aspects, results of the determination of the one or more properties may be presented to a user or operator of the core flooding system 100 through a graphical user interface (GUI) of the control system 999.

Figure 2A:
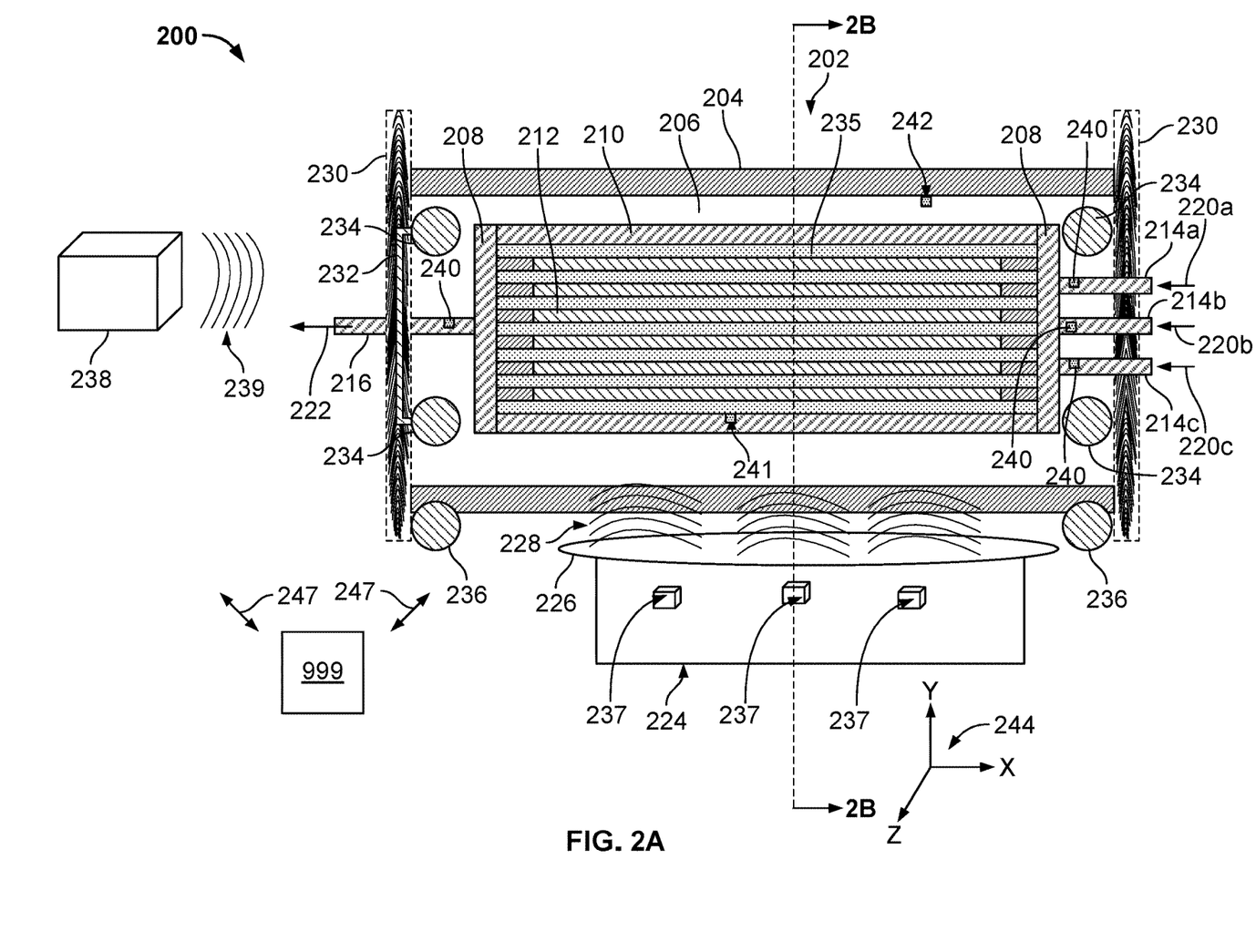
FIGS. 2A-2B are side and end views, respectfully, of another example implementation of a core flooding system according to the present disclosure.
Figure 2B:
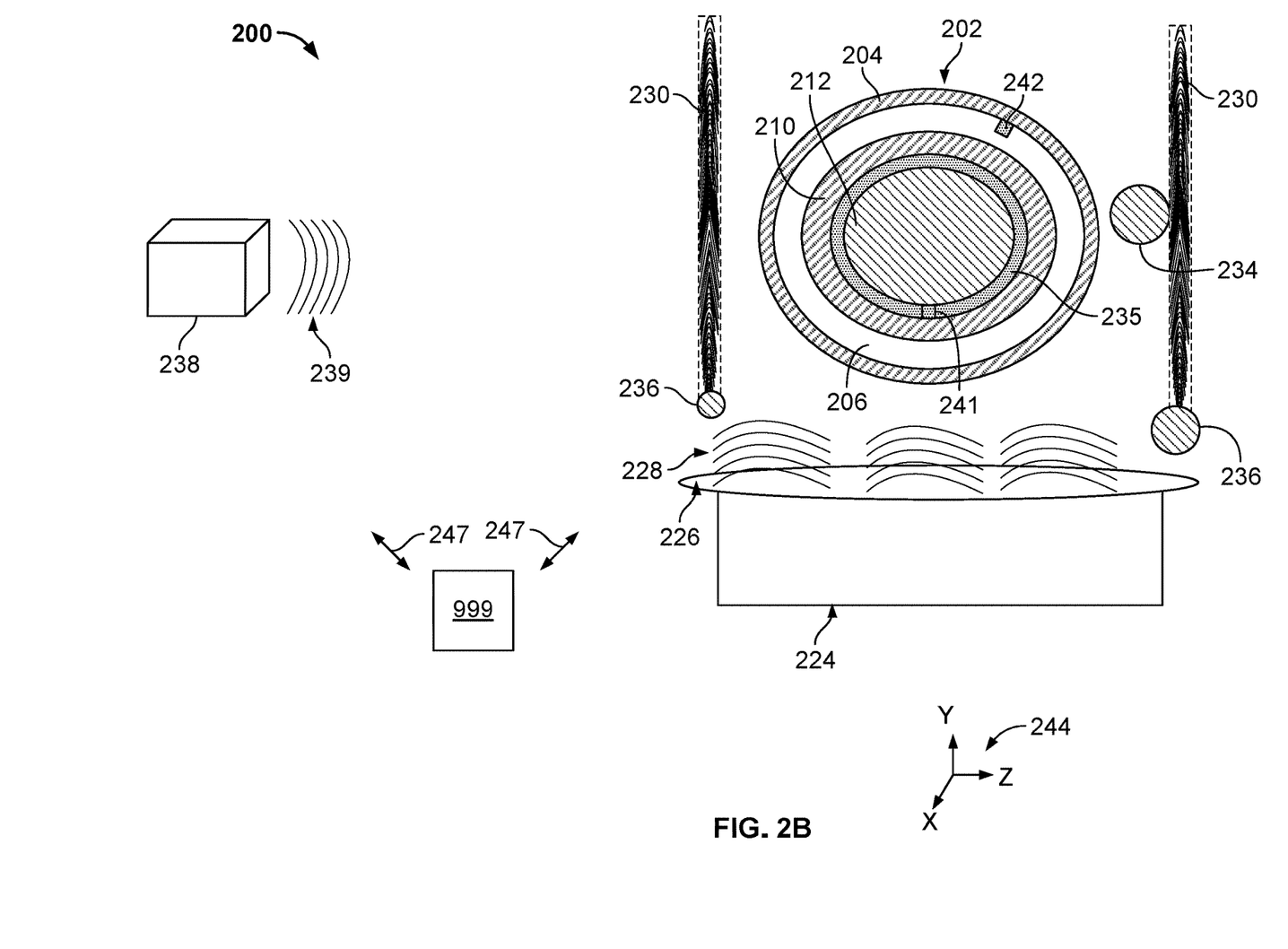

FIGS. 2A-2B are side and end views, respectfully, of another example implementation of a core flooding system 200 according to the present disclosure. Generally, the core flooding system 200 may operate to analyze a core sample 212, as well as a fluid flow through the core sample 212, under various and varying conditions, including a wide range of vibrational frequencies, acoustic wave energy, rotation and tilting, and convention varying conditions such as temperature and pressure. In some aspects, the use of vibration to improve oil recovery has been implemented, with successful vibration stimulation in shallow reservoirs with high water oil ratios (WOR). Laboratory and pre-pilot field-testing of a vibration impact, for example, to simulate such conditions, has been lacking. The core flooding system 200 implements such conditions using vibro-seismic technology that generates vibrational energy, acoustic wave energy, or both.

As shown in this example implementation, the core flooding system 200 includes a core holder 202 that is comprised of a housing 204 (for example, a cylindrical housing) that may be enclosed on open ends by end plates 208 (or core plugs 208) to define an inner volume 206. The core sample 212 may be inserted into the inner volume 206 (and enclosed there by the housing 204 and the plates or plugs 208). In some aspects, as shown, a sleeve 210 (for example, a flexible sleeve) may be used to hold the core sample 212 in the inner volume 206.

In this example, multiple fluid inlets 214*a*, 214*b*, and 214*c* are positioned through one end plate 208 while a fluid outlet 216 is positioned through another end plate 208. In this example, a different fluid 220*a*, 220*b*, and 220*c* may be circulated through each respective inlet 214*a*-214*c*. For example, in some aspects, fluid 220*a* may be water, fluid 220*b* may be oil, and fluid 220*c* may be gas. The fluids 220*a*-220*c* are circulated to the core sample 212, in which they may mix or flow there through in separate paths to be combined in an outlet fluid 222. Although note shown in this example, one or more valves may be positioned on one or both of the inlet 214 and the outlet 216 to control a flow of the fluids 220*a*-220*c* and the outlet fluid 222. The valves, in some aspects, may be controlled by control system 999 shown in these figures.

Like conventional core flooding systems, the core flooding system 200 may conduct core flooding and interfacial tension contact angle tests that mimic reservoir conditions (for example, pressure, temperature, and reservoir fluids). In some aspects, the core flooding system 200 may apply a constant pressure across the end plates 208 or constant flow through the end plates 208 (or core plugs 208). Core flood tests can be conducted using single or multiple core holders to acquire critical reservoir properties such as permeability contrasts and fluid movement in porous media. Core flooding results may then be used to guide mathematical models and extract critical simulation parameters.

While helpful, such conventional tests (which still may be performed by the core flooding system 200), may not take into consideration an impact of natural or imposed seismic activities as well as surface vibrations by heavy equipment. As shown in FIGS. 2A-2B, the system 200 may include multiple acoustic vibration sub-assemblies, each of which may be operated to generate and transmit vibration and/or acoustic energy to the core holder 202, either sequentially or together. For example, system 200 includes mechanical vibrator 224 that may be communicably coupled to the control system 999. In some aspects, the mechanical vibrator 224 may be operated (for example, by the control system 999) to generate vibration energy 228 and transmit the generated vibration energy 228 to the core holder 202 (for example, directly to the core holder 202 through direct contact). In some aspects, such direct vibration energy transmitted by the mechanical vibrator 224 may mobilize oil or other hydrocarbon fluid that is trapped (stationary) within the core sample 212 during testing.

As shown in this example, a plate 226 may be mounted to the mechanical vibrator 224 and operated (for example, by the control system 999) to rotate about one or more axes (such as one or more of the axes in the x-y-z coordinate system 244 shown in FIG. 2A). The core holder 202 may be coupled to the plate 226 during operation, thereby allowing for rotation of the core holder 202 and the core sample 212 during testing. In some aspects, as shown, one or more springs 237 may be positioned between the mechanical vibrator 224 and the plate 226 to transmit or even enhance the vibration energy 228 provided to the core holder 202.

As shown in this example, system 200 includes another acoustic vibration sub-assembly in the form of rods 230 that are mounted at axial ends of the core holder 202 as shown. In this example, each of the rods 230 include an airflow path 232 (shown as an example on one of the rods 230) that, for instance, is internal to the rods 230. One or more balloons 234 (two for each rod 230 in this example) are fluidly coupled to the airflow paths 232 of the rods 230, for example, through one or more perforations in the rods 230. Airflow from an airflow source (not shown) may be circulated (for example, by the control system 999) through the airflow paths 232 to inflate the balloons 234 in order to induce a direct vibration energy on the core holder 202. For instance, by sequentially inflating and deflating the balloons 234 (and varying the relative inflation of each of the balloons), the direct vibration energy (for example, both axial and radial energy relative to the position of the core sample 212) may be generated and transmitted to the core holder 202 and thus the core sample 212 during testing. In some aspects, such direct vibration energy transmitted by the balloons 234 may mobilize oil or other hydrocarbon fluid that is trapped (stationary) within the core sample 212 during testing.

As shown in this example, system 200 includes another acoustic vibration sub-assembly in the form of an acoustic vibrator 235 that is positioned between the sleeve 210 and the core sample 212. In some aspects, the acoustic vibrator 235 may be operated (for example, by the control system 999) to generate acoustic wave energy (for example, electromagnetic wave energy similar to EM logging tools) directly to the core sample 212 during testing. In some aspects, such direct acoustic wave energy transmitted by the acoustic vibrator 235 may act on an interface of the different fluids or emulsion layer within the core sample 212 and separate suspended oil bubbles within water to help mobilize trapped oil within the core sample 212 during testing.

As further shown in this example, system 200 includes another acoustic vibration sub-assembly in the form of an acoustic noise source 238 that is positioned remotely from (for example, not in direct contact with) the core holder 202. The acoustic noise source 238 may be operated (for example, by the control system 999) to generate acoustic wave energy 239 (for instance, a seismic wave that replicates seismic wave sources used to examine a reservoir formation) and transmit such acoustic wave energy 239 to the core holder 202 and thus to the core sample 212. In some aspects, such indirect acoustic wave energy transmitted by the acoustic noise source 238 may help evaluate a change in oil recovery due to seismic energy during testing of the core sample 212.

As shown in this example, one or more inflatable balloons 236 may be positioned at ends of the core holder 202, such as at interfaces between the core holder 202 and the rods 230. In this example, there may be four inflatable balloons 236 positioned at four corner interfaces of the core holder 202 and the rods 230 (as there may be four rods 230 used in the system 200). Each of the inflatable balloons 236 may be independently inflatable with an airflow source (not shown) by the control system 999 to tilt the core holder 202 about any of the axes in the x-y-z coordinate system 244, either alone or in combination. For instance, as shown in FIG. 2B, one of the inflatable balloons 236 (on the right side of the figure) is more inflated than another of the balloons 236 (on the left side of the figure), thereby causing the core holder 202 to tilt about the x-axis.

In some aspects, operation of any combination of the inflatable balloons 236, the rotational plate 226, the mechanical vibrator 224, the acoustic vibrator 235, the rods 230/balloons 234, and the acoustic noise source 238 may occur simultaneously or sequentially. Thus, a single, two, three, or more of these described features of the core flooding system 200 may be operated in any combination together or in series. Further, in some aspects, changes in temperature, pressure, or both, within the inner volume 206 (and thus the core sample 212) may be made in parallel with or sequentially with these described features of the core flooding system 200. Still further, changes in properties of the fluid 220 (for example, composition, pressure, temperature, and otherwise) may be made in parallel with or sequentially with operation of these described features of the core flooding system 200, as well as in parallel with or sequentially with other conventional testing parameters (for example, temperature or pressure).

As shown in this example, the core flooding system 200 includes one or more fluid sensors 240 (in this case, one on each inlet 214*a*-214*c* and another on the outlet 216), as well as other sensors 241 and 242. In some aspects, each sensor shown in FIGS. 2A-2B may represent one or multiple sensors. Each sensor shown in FIGS. 2A-2B may also be an analog or digital sensor. In some aspects, the illustrated sensors 240, 241, and 242 may be fiber optic conductors.

As shown in this example, one or more sensors 242 may be positioned within the internal volume 206 (but external to the sleeve 210). Further, in this example implementation, one or more sensors 241 may be positioned between the core sample 212 and the sleeve 210. Alternatively, sensors may be placed external to (for example, in contact with an exterior surface of) the housing 204.

The example implementation of the core flooding system 200 includes a control system 999. In some implementations, the control system 999 is a microprocessor-based control system that includes one or more hardware processors, one or more memory modules communicably coupled to the hardware processor(s), and instructions and data encoded on the one or more memory modules. The hardware processor(s) are operable to execute the instructions to perform operations, including operations described in the present disclosure. As shown in this example (for instance, by the bi-directional arrows 247), the control system 999 may be communicably coupled (wired or wirelessly) to, for instance, the inflatable balloons 236 (for example, an airflow source fluidly coupled to the balloons 236), the rotational plate 226, the mechanical vibrator 224, the acoustic vibrator 235, the rods 230/balloons 234 (for example, an airflow source fluidly coupled to the balloons 236), and the acoustic noise source 238. In some aspects, the control system 999 may receive data from the such components, as well as the sensors 240, 241, and 242. The control system 999 may also provide commands (pre-programmed or otherwise) to the inflatable balloons 236 (for example, an airflow source fluidly coupled to the balloons 236), the rotational plate 226, the mechanical vibrator 224, the acoustic vibrator 235, the rods 230/balloons 234 (for example, an airflow source fluidly coupled to the balloons 236), and the acoustic noise source 238.

For example, in an example operation, the control system 999 may command one or more of the mechanical vibrator 224, the acoustic vibrator 235, the rods 230/balloons 234 (for example, an airflow source fluidly coupled to the balloons 236), and the acoustic noise source 238 to generate and transmit the vibration and/or acoustic wave energy 228, 239, or other energy to the core holder 202 (and thus the core sample 212). For example, two or more of such components can be operated in combination depending on, for example, a type of the core sample 212, as well as wave signature and intensity derived from the relevant field from which the core sample 212 was collected. Thus, in some aspects, the core flooding system 200 may operate to downscale field scale waves to a lab-level approach and create a comparable range of such waves. In some aspects, waves signatures may also depend on the source of waves in the field (for example, tectonic movement, earthquake, from seismic truck, from injection or hydraulic fracturing) to be emulated by the core flooding system 200. Also, depending on a clarity of the wave signature and ability of differentiating them from the field, multiple energy waves can be combined during operation of the core flooding system 200.

The control system 999 may also command at least one of the inflatable balloons 236 (for example, an airflow source fluidly coupled to the balloons 236) or the rotational plate 226, either simultaneous with or sequentially with the operation of the components that generate vibration and/or acoustic wave energy. The control system 999 may also command one or more valves fluidly coupled to the inlets 214a-214c and the outlet 216 to facilitate circulation of the fluids 220a-220c into the inner volume 206 of the core holder 202 (and thus to the core sample 212), either simultaneous with or sequentially with the operation of the rotation and vibration/acoustic energy components. Further, the control system 999 may operate to adjust a temperature or pressure within the inner volume 206.

The sensors 240, 241, and/or 242 may measure one or more parameters associated with the core sample 212, such as temperatures, confining stresses (for example, to mimic reservoir confining stress when subjected to different acoustic or seismic energy waves), pressures, fluid content, directional flow (for example, velocity, pathways, or both) of one or more phases of a multiphase fluid, and other parameters. In some aspects, for instance, movement (for instance, rotation, tilting, vibration) of the core holder 202 in different directions can affect the evaluation of directional permeability, vertical permeability (such as in tilted reservoirs) and can evaluate gravity drainage effects on remaining oil saturation (SOR) and additional hydrocarbon recovery in a reservoir.

Based on such measurements, the control system 999 may determine one or more properties of the core sample 212, and also a reservoir formation from which the core sample 212, was taken. Such properties include, for example, porosity, grain density, directional permeability, and other properties. In some aspects, results of the determination of the one or more properties may be presented to a user or operator of the core flooding system 100 through a graphical user interface (GUI) of the control system 999.

In some aspects, in some aspects, X-ray attenuation can be attached to the core holder 202 or on the core sample 212 to monitor the in situ saturation of each fluid 220a-220c across the core sample 212. Sensors 241, therefore, can measure the attenuation in order for a determination of preferred paths for each fluid 220a-220c. As another example of determining fluid pathways, as the core holder 212 is tilted or rotated, gravity segregation of the fluids 220a-220c may occur, and the heavier fluid(s) will follow a path through the core sample 212 lower (for example, closer to ground) than lighter fluid(s). Deviations from such pathways by the fluids 220a-220c may indicate the existence of heterogeneity.

In still further aspects, sensors fluidly coupled to the inlets 214a-214c may determine compositions, flow rates, temperatures, and pressures of the fluids 220a-220c. Such sensors may provide an initial set of data for the input fluids 220a-220c that can then be compared (for example, by the control system 999) to measurements (compositions, flow rates, temperatures, and pressures) of the fluids 220a-220c as they mix and flow through the core sample 212 by the sensors 241). Such comparisons may be used to determine (for example, by the control system 999) fluid pathway information, as well as properties of the core sample 212 such as permeability, porosity, and others.

Figure 3:
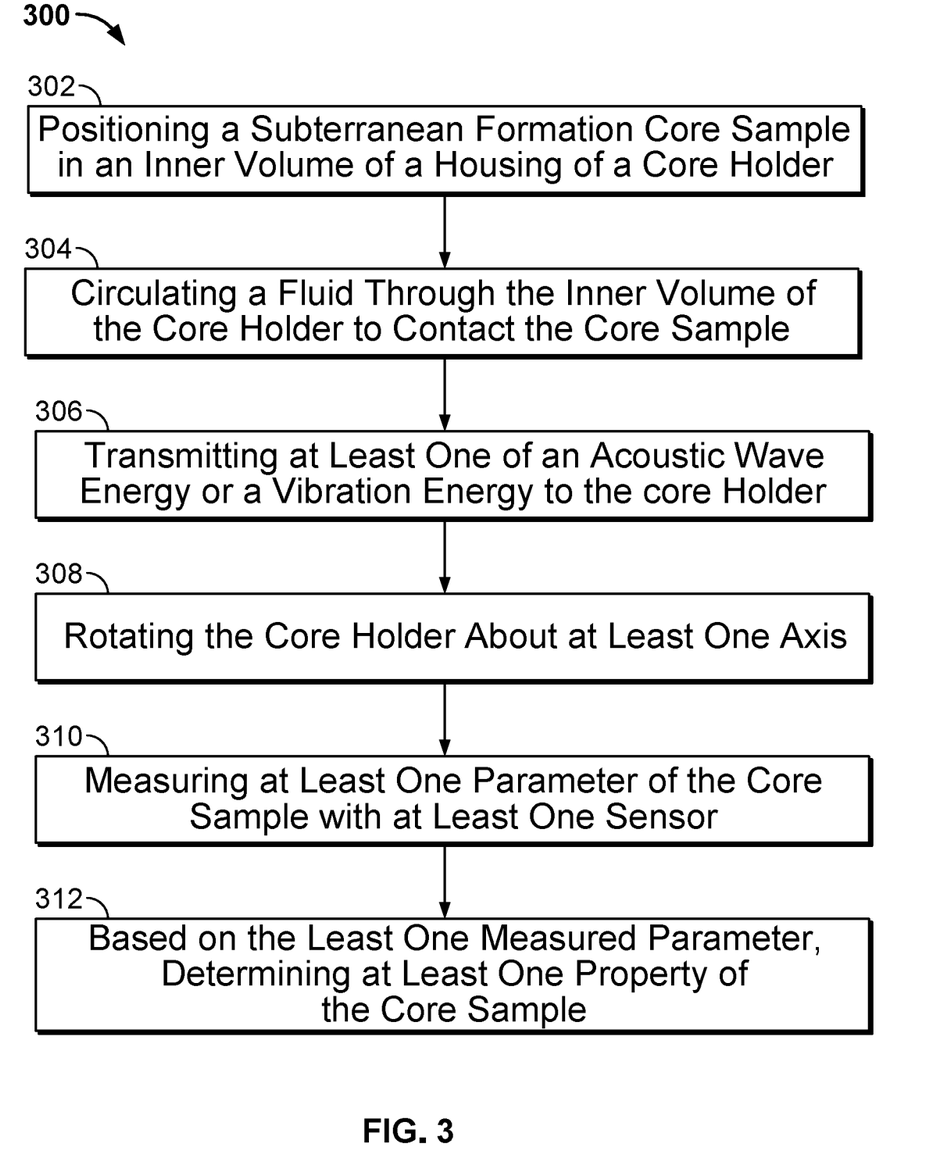
FIG. 3 is a flowchart that describes an example method performed with a core flooding system according to the present disclosure.

FIG. 3 is a flowchart that describes an example method 300 performed with a core flooding system according to the present disclosure. In some aspects, method 300 may be performed with either of the core flooding system 100 or the core flooding system 200 shown in this disclosure. Method 300 may begin at step 302, which includes positioning a subterranean formation core sample in an inner volume of a housing of a core holder. For example, a core sample may be inserted into a volume of a core holder of a core flooding system and, in some aspects, into a sleeve that is positioned in the volume. The volume may be sealed to an ambient environment but with at least one fluid inlet and at least one fluid outlet that fluidly couple the volume to a source of one or more fluids (such as oil, gas, water). The core flooding system can include sensors (such as fiber optic sensors) positioned in various locations, such as in the inlet and/or outlet, within the volume, in contact with the core holder, or between the sleeve and the core sample, as some examples.

Method 300 may continue at step 304, which includes circulating a fluid through the inner volume of the core holder to contact the core sample. For example, a mixture of oil, gas and water, or even separate streams of oil, gas, and water, can be circulated into the volume through the inlet, and circulated out of the volume (for example, in a continuous or semi-continuous stream) through the outlet. One or more valves may be operated to circulate the fluid through the volume to contact and, in some cases, saturate, the core sample. In some aspects, one or more pumps may also be operated to circulate the fluid through the volume to contact and, in some cases, saturate, the core sample.

Method 300 may continue at step 306, which includes transmitting at least one of an acoustic wave energy or a vibration energy to the core holder. For example, the core flooding system may include one or multiple sub-assemblies operable to generate and transmit one or both of vibration energy or acoustic wave energy. In some aspects, one or more sub-assemblies may be in direct contact with the core sample and generate and transmit one or both of vibration energy or acoustic wave energy directly to the core sample. In some aspects, one or more sub-assemblies may be in indirect contact with the core sample (for example, in contact with a component of the core flooding system that is in contact with the core sample) and generate and transmit one or both of vibration energy or acoustic wave energy indirectly to the core sample. In some aspects, one or more sub-assemblies may be remote the core sample and generate and transmit one or both of vibration energy or acoustic wave energy to the core sample through an ambient environment.

Method 300 may continue at step 308, which includes rotating the core holder about at least one axis. For example, the core flooding system may include one or more rotation sub-assemblies that operate to tilt or rotate the core holder, and thus core sample, about one or more axes of a three-dimensional coordinate system. For example, a core sample, often being cylindrical in shape, may be rotated about a centerline radial axis. The core sample may also be rotated or tilted about one or more axes that extend through a diameter of the core sample (and are orthogonal to the radial axis). In some aspects, steps 304 through 308 may be performed in a different order or may be performed (and continue to be performed) simultaneously). In some aspects, step 304 or step 308 may not be part of method 300.

Method 300 may continue at step 310, which includes measuring at least one parameter of the core sample with at least one sensor. For example, as the core sample is receiving or has received the circulated fluid, and as the core sample is receiving the transmitted vibration or acoustic wave energy, and as the core sample is being rotated or tilted, sensors of the core flooding system may take one or more measurements. Such measurements may be, for example, fluid composition, fluid pressure, fluid temperature, core sample temperature, core sample pressure, gamma or X-ray attenuation, contact angle, interfacial tension, and other parameters. Such measurements may be provided by the sensor(s) to a control system that is part of or coupled to the core flooding system.

Method 300 may continue at step 312, which includes based on the at least one measured parameter, determining at least one property of the core sample. For example, the control system may determine properties of the core sample such as fluid flow pathways (and other properties, such as velocity, of the fluid(s) flowing through the core sample), permeability, porosity, as well as others. In some aspects, the measure values, as well as the determined property (or properties) may be presented to a user on a GUI of the control system. Such property determinations may allow for further determinations. For example, decisions and designs of future oil recovery (EOR) processes, injectivity, and water shut off jobs may be better informed due to the determinations made in step 312. As another example, the core flooding system may better assess certain parameters (such as interfacial tension and contact angle) that are helpful for hydrocarbon reserve evaluation and fluids distribution in oil and gas reservoirs as compared to conventional techniques based on the determinations made in step 312. Thus, the determinations made in step 312 may allow for greater time and resource efficiencies associated with well completions by providing more accurate reservoir information based on the tested core sample.

Figure 4:
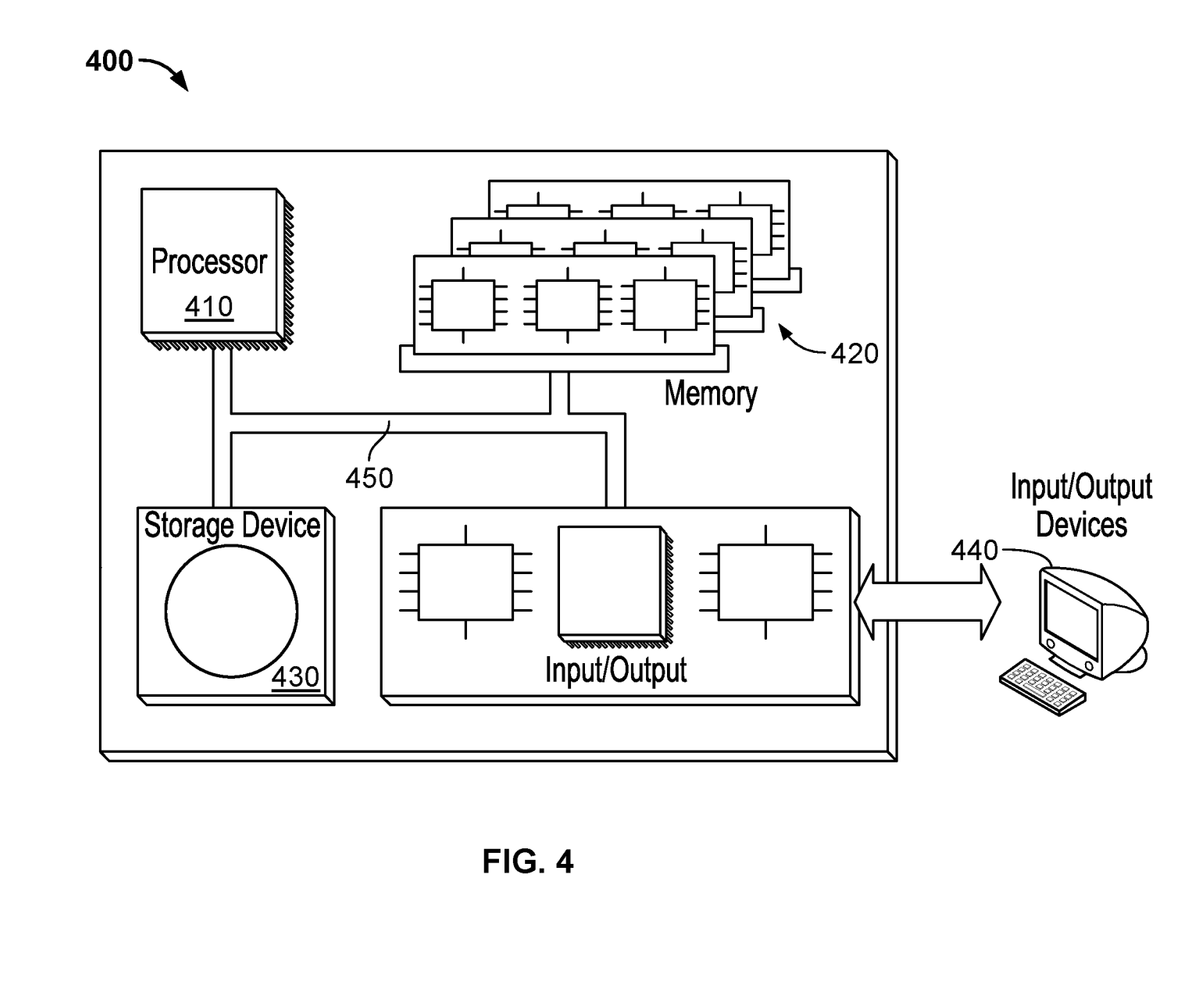
FIG. 4 is a schematic illustration of an example controller (or control system) for controlling operations of a core flooding system according to the present disclosure

FIG. 4 is a schematic illustration of an example controller 400 (or control system) for controlling operations of a core flooding system according to the present disclosure. For example, the controller 400 may include or be part of the control system 999 shown in FIGS. 1 and 2A-2B. The controller 400 is intended to include various forms of digital computers, such as printed circuit boards (PCB), processors, digital circuitry, or otherwise that is part of a core flooding system. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 400 includes a processor 410, a memory 420, a storage device 430, and an input/output device 440. Each of the components 410, 420, 430, and 440 are interconnected using a system bus 450. The processor 410 is capable of processing instructions for execution within the controller 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the controller 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the controller 400. In one implementation, the storage device 430 is a computer-readable medium. In various different implementations, the storage device 430 may be a floppy disk device, a hard disk device, an optical disk device, or a tape device.

The input/output device 440 provides input/output operations for the controller 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for testing a core sample, comprising:
    positioning a subterranean formation core sample in an inner volume of a core holder, the core holder comprising a housing that defines the inner volume, a fluid inlet, and a fluid outlet;
    transmitting at least one of an acoustic wave energy or a vibration energy to the core holder, wherein the transmitting comprises:
        flowing a fluid through an airflow path of at least one perforated rod coupled to the core holder,
        inflating at least one balloon fluidly coupled to the airflow path through the perforated rod, and
        based on inflating the at least one balloon, transmitting at least one of the acoustic wave energy or the vibration energy to the core holder;
    during the transmission of the at least one of the acoustic wave energy or the vibration energy to the core holder, measuring at least one parameter of the core sample with at least one sensor coupled to the core holder or positioned in the inner volume of the core holder; and
    based on the at least one measured parameter, determining at least one property of the core sample.

2. The method of claim 1, wherein the transmitting further comprises:
    transmitting at least one of an acoustic wave energy or a vibration energy to an outer radial surface of the core holder and through the outer radial surface to the core sample.

3. The method of claim 1, further comprising:
    modulating at least one valve fluidly coupled to at least one of the fluid inlet or the fluid outlet; and
    circulating a fluid through the inner volume of the core holder to contact the core sample.

4. The method of claim 3, further comprising rotating the core holder about an axis with at least one rotating plate to which the core holder is mounted.

5. The method of claim 1, further comprising rotating the core holder about an axis with at least one rotating plate to which the core holder is mounted.

6. The method of claim 5, wherein the axis comprises a first axis, the method further comprising rotating the core holder about a second axis with the at least one rotating plate.

7. The method of claim 6, wherein rotating the core holder about the first and second axes occurs simultaneously.

8. The method of claim 1, further comprising, while transmitting at least one of the acoustic wave energy or the vibration energy to the core holder:
    inflating at least one balloon mounted to the core holder; and
    based on inflating the at least one balloon, tilting the core holder.

9. The method of claim 8, further comprising:
    modulating at least one valve fluidly coupled to at least one of the fluid inlet or the fluid outlet; and
    circulating a fluid through the inner volume of the core holder to contact the core sample.

10. The method of claim 8, further comprising rotating the core holder about an axis with at least one rotating plate to which the core holder is mounted.

11. The method of claim 10, wherein the axis comprises a first axis, the method further comprising rotating the core holder about a second axis with the at least one rotating plate.

12. The method of claim 11, wherein rotating the core holder about the first and second axes occurs simultaneously.

13. A method for testing a core sample, comprising:
positioning a subterranean formation core sample in an inner volume of a core holder, the core holder comprising a housing that defines the inner volume, a fluid inlet, and a fluid outlet;
transmitting at least one of an acoustic wave energy or a vibration energy to the core holder;
while transmitting at least one of the acoustic wave energy or the vibration energy to the core holder:
inflating at least one balloon mounted to the core holder, and
based on inflating the at least one balloon, tilting the core holder;
during the transmission of the at least one of the acoustic wave energy or the vibration energy to the core holder, measuring at least one parameter of the core sample with at least one sensor coupled to the core holder or positioned in the inner volume of the core holder; and
based on the at least one measured parameter, determining at least one property of the core sample.

14. The method of claim 13, wherein the transmitting further comprises:
transmitting at least one of an acoustic wave energy or a vibration energy to an outer radial surface of the core holder and through the outer radial surface to the core sample.

15. The method of claim 13, further comprising:
modulating at least one valve fluidly coupled to at least one of the fluid inlet or the fluid outlet; and
circulating a fluid through the inner volume of the core holder to contact the core sample.

16. The method of claim 15, wherein the transmitting further comprises:
transmitting at least one of an acoustic wave energy or a vibration energy to an outer radial surface of the core holder and through the outer radial surface to the core sample.

17. The method of claim 13, further comprising rotating the core holder about an axis with at least one rotating plate to which the core holder is mounted.

18. The method of claim 17, wherein the axis comprises a first axis, the method further comprising rotating the core holder about a second axis with the at least one rotating plate.

19. The method of claim 18, wherein rotating the core holder about the first and second axes occurs simultaneously.

20. The method of claim 15, further comprising rotating the core holder about an axis with at least one rotating plate to which the core holder is mounted.

21. The method of claim 20, wherein the axis comprises a first axis, the method further comprising rotating the core holder about a second axis with the at least one rotating plate.

22. The method of claim 21, wherein rotating the core holder about the first and second axes occurs simultaneously.

23. A core sample test apparatus, comprising:
a housing sized to receive a core sample that comprises a portion of a hydrocarbon reservoir formation;
means for generating at least one of an acoustic wave energy or a vibration energy to the core holder;
at least one sensor positioned to detect a change in at least one parameter of the core sample during operation of the means for generating the at least one of the acoustic wave energy or the vibration energy; and
a control system communicably coupled to the at least one sensor and configured to receive the change in the at least one parameter of the core sample and determine at least one property of the hydrocarbon reservoir formation, the at least one property of the hydrocarbon reservoir formation comprising at least one of:
a permeability of the hydrocarbon reservoir formation;
a brine permeability of the hydrocarbon reservoir formation; or
a porosity of the hydrocarbon reservoir formation.

24. The core sample test apparatus of claim 23, further comprising means for rotating the core sample, the control system operably coupled to the means for generating and the means for rotating.

25. The core sample test apparatus of claim 23, wherein the sensor comprises a fiber optic conductor mounted within a sleeve that is configured to hold the core sample in the housing.

26. The core sample test apparatus of claim 23, wherein the control system is operably coupled to the means for generating.

27. The core sample test apparatus of claim 23, wherein the means for generating comprises means for generating the at least one of the acoustic wave energy or the vibration energy to an outer radial surface of the core holder and through the outer radial surface to the core sample.

28. The core sample test apparatus of claim 23, wherein the at least one parameter of the core sample comprises at least one of:
a flow rate of a fluid through the core sample;
an interfacial tension;
a contact angle between a fluid and the core sample;
a fluid path of water or brine through the core sample; or
a fluid path of a hydrocarbon through the core sample.

29. The core sample test apparatus of claim 28, further comprising means for rotating the core sample.

30. The core sample test apparatus of claim 29, wherein the control system is operably coupled to the means for rotating.

* * * * *